United States Patent [19]

Tsuji et al.

[11] Patent Number: 4,592,868
[45] Date of Patent: Jun. 3, 1986

[54] 11-HYDROXYPREGN-4-EN-3-ONE-20-CARBALDEHYDE AND A METHOD FOR ITS PRODUCTION

[75] Inventors: Masao Tsuji; Fumio Mori; Yoshihiro Ichihara, all of Kurashiki, Japan

[73] Assignee: Kuraray Co., Ltd., Kurashiki, Japan

[21] Appl. No.: 607,458

[22] Filed: May 7, 1984

[30] Foreign Application Priority Data

May 9, 1983 [JP] Japan .................................. 58-81235

[51] Int. Cl.$^4$ ........................... C07B 29/02; C07J 9/00
[52] U.S. Cl. .................................... 260/397.1; 435/53; 435/52; 435/829; 435/253
[58] Field of Search ....................... 260/397.4 S, 397.1

[56] References Cited

U.S. PATENT DOCUMENTS 4,175,006 11/1979 Wovcha et al. ..................... 195/51
4,405,525 9/1983 Knight et al. ................... 260/397.1

OTHER PUBLICATIONS

Chem. Abstracts (1985) 102 (11) Par. 94329p.

Primary Examiner—Elbert L. Roberts
Attorney, Agent, or Firm—Burns, Doane, Swecker & Mathis

[57] ABSTRACT

There is provided the novel compound 11-hydroxypregn-4-en-3-one-20-carbaldehyde, as well as a microbial method for production of the same. This novel compound is of value as a starting material for antiinflammatory corticoids such as hydrocortisone, cortisone, prednisolone and prednisone.

2 Claims, No Drawings

11-HYDROXYPREGN-4-EN-3-ONE-20-CARBALDEHYDE AND A METHOD FOR ITS PRODUCTION

BACKGROUND OF THE INVENTION

1. Field of the Invention

This invention relates to 11-hydroxypregn-4-en-3-one-20-carbaldehyde of the formula

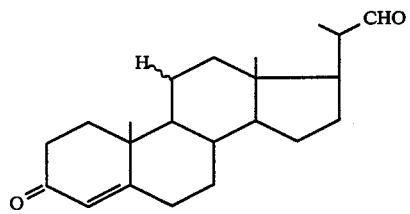

wherein the wavy line ∼ denotes that the indicated hydroxy group is either in the α- or in the β-configuration, and a microbial method for producing the same.

2. Description of the Prior Art

11-Hydroxypregn-4-en-3-one-20-carbaldehyde, hereby provided in accordance with this invention, is a novel compound which has not been described in the literature up to this day. The compound is obtainable by permitting a selected strain of microorganism to act upon 11-hydroxylithocholic acid or/and a salt thereof, and is of value as a starting compound for the synthesis of corticoids having potent antiinflammatory activity such as hydrocortisone, cortisone, prednisolone and prednisone.

For the production of prednisone, for instance, there is known a process which involves twenty-odd steps starting with deoxycholic acid [L. F. Fieser & M. Fieser: Steroids, Reinhold Publishing Corporation, 1959, pp. 634–647] but since this process requires use of costly reactants and reagents and a long series of production steps, it is not much suitable for commercial production.

SUMMARY OF THE INVENTION

It is an object of this invention to provide the novel compound 11-hydroxypregn-4-en-3-one-20-carbaldehyde which is of value as a starting material for the synthesis of various corticoids.

It is another object of this invention to provide the novel compound 11-hydroxypregn-4-en-3-one-20-carbaldehyde which is of value as a starting material for the synthetic production of hydrocortisone, cortisone, prednisolone or prednisone.

It is a still further object of this invention to provide a microbial method for producing the novel and useful 11-hydroxypregn-4-en-3-one-20-carbaldehyde.

These objects as well as other objects and advantages of the present invention will become apparent to those skilled in the art from the following detailed description.

11-Hydroxypregn-4-en-3-one-20-carbaldehyde is the object compound provided in accordance with this invention. Also provided is a method for producing 11-hydroxypregn-4-en-3-one-20-carbaldehyde which comprises cultivating a strain of microorganism of the genus Alcaligenes, which is able to utilize 11-hydroxylithocholic acid or/and a salt thereof as the substrate to elaborate 11-hydroxypregn-4-en-3-one-20-carbaldehyde, in a medium containing said 11-hydroxylithocholic acid or/and a salt thereof.

DETAILED DESCRIPTION OF THE INVENTION

The microorganism to be used in the present invention may be a wild strain of the genus Alcaligenes or a mutant thereof, which is derived by spontaneous mutation or by a conventional mutagenic treatment such as X-ray irradiation, ultraviolet irradiation, treatment with a chemical mutagen such as N-methyl-N'-nitro-N-nitrosoguanidine, 4-nitroquinoline-N-oxide, acriflavine or ethyl methanesulfonate, or by a combination thereof and the like.

Among the microorganisms capable of producing 11-hydroxypregn-4-en-3-one-20-carbaldehyde by utilizing 11-hydroxylithocholic acid or a salt thereof as the substrate, a representative strain has been deposited with the Fermentation Research Institute, Agency of Industrial Science and Technology, Japan (hereinafter, referred to as FERM). It is the strain *Alcaligenes faecalis* D4020-K15 (FERM BP-204). *Alcaligenes faecalis* D4020-K15 is a mutant of *Alcaligenes faecalis* D4020 (FERM BP-182) which is a wild strain isolated from soil.

The morphological, cultural and physiological characteristics of these strains are shown in the following Table.

TABLE

| Taxonomical character | *Alcaligenes faecalis* D4020 | *Alcaligenes faecalis* D4020-K15 |
|---|---|---|
| Morphological characteristics | | |
| Form | Rods | Rods |
| Size | 0.5 × 1.2∼1.7μ | 0.5 × 1.0∼1.7μ |
| Flagellum | *Peritrichous flagella* | *Peritrichous flagella* |
| Spore | Nil | Nil |
| Gram stain | Negative | Negative |
| Acid fast stain | Nil | Nil |
| Cultural characteristics | | |
| Bouillon agar plate culture | Circular, opaque, convex | Circular, opaque, convex |
| Bouillon agar slant culture | Moderate growth, filiform, pigment not produced | Moderate growth, filiform, pigment not produced |
| Bouillon broth | Moderate turbidity, pellicle | Moderate turbidity |
| Temperature for growth | Growth at 37° C., poor growth at 41° C. | Growth at 37° C., poor growth at 41° C. |
| Gelatin stab | No liquefaction | No liquefaction |
| Litmus milk | Alkaline, milk unchanged | Alkaline, milk unchanged |
| BCP milk | Alkaline, milk unchanged | Alkaline, milk unchanged |
| Physiological characteristics (Note 1) | | |

TABLE-continued

| | | | | |
|---|---|---|---|---|
| Nitrate reduction | + | | + | |
| Denitrification | − | | − | |
| Methyl red test | − | | − | |
| Voges-Proskauer test | − | | − | |
| Indole production | − | | − | |
| Hydrogen sulfide production | − | | − | |
| Starch hydrolysis | − | | − | |
| Citrate utilization | + | | + | |
| Assimilation of inorganic nitrogen sources | + | | + | |
| Urease | ± | | ± | |
| Oxidase | + | | + | |
| Catalase | + | | + | |
| Require of oxygen | Aerobic | | Aerobic | |
| Oxidation/Fermentation test | Oxidative | | Oxidative | |
| Production of acids and gases from carbohydrates (Note 2) | Production of acids | Evolution of gases | Production of acids | Evolution of gases |
| (1) L-Arabinose | + | − | + | − |
| (2) D-Xylose | + | − | + | − |
| (3) D-Glucose | + | − | + | − |
| (4) D-Mannose | + | − | + | − |
| (5) D-Fructose | − | − | − | − |
| (6) D-Galactose | + | − | + | − |
| (7) Maltose | − | − | − | − |
| (8) Sucrose | − | − | − | − |
| (9) Lactose | − | − | − | − |
| (10) Trehalose | − | − | − | − |
| (11) D-Sorbitol | − | − | − | − |
| (12) D-Mannitol | − | − | − | − |
| (13) Inositol | − | − | − | − |
| (14) Glycerol | − | − | − | − |
| (15) Starch | − | − | − | − |

Remarks:
(Note 1) The symbols used under Physiological characteristics indicate the following:
+: The strain has the corresponding characteristics or produces the corresponding product.
±: It is difficult to determine whether the strain has the corresponding characteristics or produces the corresponding product or not.
−: The strain neither has the corresponding characteristics nor produces the corresponding product.
(Note 2) By using Hugh and Leifson medium in which each of the carbohydrates shown in Table was used in lieu of the carbon source thereof, production of acids and gases by the strain was observed.
+: An acid or a gas is produced.
±: It is difficult to determine whether an acid or a gas is produced or not.
−: Neither an acid nor a gas is produced.

On the basis of these morphological, cultural and physiological characteristics, the strains have been classified according to Bergey's Manual of Determinative Bacteriology, 7th and 8th Editions.

The strain Alcaligenes faecalis D4020 has been identified as a strain of the genus Alcaligenes based on its morphological characteristics, among others, that it is a rod having peritrichous flagella and that it reacts negative in Gram staining as well as on the physiological characteristics, among others, that it reacts positive in the oxidase and catalase reactions, that it is aerobic and that the oxidation/fermentation test gives oxidative results, and further identified as a strain of the species Alcaligenes faecalis based on the facts that it does not liquefy gelatin, that milk becomes alkaline but otherwise remains unchanged and that it does not cause denitrification. Generally, a mutant is considered to belong to the same species as its parent strain belongs to. Accordingly, the strain Alcaligenes faecalis D4020-K15 has been judged as belonging to the species Alcaligenes faecalis.

The production of 11-hydroxypregn-4-en-3-one-20-carbaldehyde in accordance with this invention is carried out by cultivating a strain of microorganism of the genus Alcaligenes, which is able to utilize 11-hydroxylithocholic acid or/and a salt thereof as the substrate to elaborate 11-hydroxypregn-4-en-3-one-20-carbaldehyde, in a medium containing said 11-hydroxylithocholic acid or/and a salt thereof. It should be understood that if 11α-hydroxylithocholic acid or/and a salt thereof is used as the substrate in the above method, 11α-hydroxypregn-4-en-3-one-20-carbaldehyde is produced as the desired compound, and if 11β-hydroxylithocholic acid or/and a salt thereof is used as the substrate, 11β-hydroxypregn-4-en-3-one-20-carbaldehyde is produced as the desired compound.

In accordance with the present invention, 11-hydroxylithocholic acid per se can be used as the substrate. There can also be used an alkali metal salt of 11-hydroxylithocholic acid such as sodium 11-hydroxylithocholate, potassium 11-hydroxylithocholate or the like. When a 11-hydroxylithocholate is used, it is dissolved in water to prepare an aqueous solution containing the 11-hydroxylithocholate in a predetermined concentration. Alternatively, a certain amount of an alkali metal compound which forms a salt with 11-hydroxylithocholic acid may previously be dissolved in water and thereto is added 11-hydroxylithocholic acid to give an aqueous solution containing a 11-hydroxylithocholate in a predetermined concentration.

In general, the concentration of the substrate in a culture medium may be varied widely in the range of from about 1 to 100 g/l as 11-hydroxylithocholic acid. However, from the viewpoints of the yield of the desired product, cultivation conditions and economic efficiency such as operability or workability, it is preferable to use the substrate in a concentration of about 2 to 50 g/l as 11-hydroxylithocholic acid.

The cultivation can be carried out according to a known method under aerobic conditions and shake or submerged culture using a liquid medium is generally employed.

As the medium, there can be used one containing nutrients which can be assimilated by the microorganism to be used. The medium may contain 11-hydroxylithocholic acid or a salt thereof as the sole carbon source. Optionally, it may contain an additional carbon source such as glucose, glycerol, peptone, meat extract, yeast extract, etc. or a mixture thereof. Generally, the additional carbon source can be added to the medium in a concentration of about 0.1 to 20 g/l. As a nitrogen source, there can be used an inorganic nitrogen source such as ammonium sulfate, ammonium chloride, ammonium phosphate, ammonium nitrate, sodium nitrate, potassium nitrate, etc.; an organic nitrogen source such as polypeptone, peptone, meat extract, etc.; or a mixture thereof. Generally, the nitrogen source can be added to the medium in a concentration of about 0.5 to 5 g/l. In addition, an inorganic salt such as dipotassium hydrogen phosphate, potassium dihydrogen phosphate, magnesium sulfate, magnesium citrate, manganese sulfate, zinc sulfate, cobalt chloride, sodium molybdate, cupric sulfate, calcium chloride, sodium chloride, etc. or a mixture thereof can be added to the medium.

The cultivation conditions are not very critical. Generally, the cultivation can be carried out in the manner of shake or submerged culture at a pH of about 7 to 9 at about 25° to 35° C. for about 10 hours to 7 days to cause production and accumulation of 11-hydroxypregn-4-en-3-one-20-carbaldehyde in the medium.

The 11-hydroxypregn-4-en-3-one-20-carbaldehyde thus accumulated in the culture broth is by far less soluble in water than the substrate 11-hydroxylithocholic acid or a salt thereof, with the result that generally it precipitates out in the broth. The harvesting and isolation of this precipitated 11-hydroxypregn-4-en-3-one-carbaldehyde can be accomplished either by the direct decantation of the liquid phase containing suspended cells or by centrifugation at a speed sufficiently low to prevent settlement of the suspended cells and subsequent decantation. After separation of the precipitated 11-hydroxypregn-4-en-3-one-20-carbaldehyde, the cells and other insoluble fractions are removed by filtration or centrifugation and the resultant filtrate or supernatant is extracted with a water-immiscible organic solvent or solvent system such as ethyl acetate, chloroform or a mixture of chloroform and methanol. Then, the solvent is evaporated from the extract to recover the 11-hydroxypregn-4-en-3-one-20-carbaldehyde remaining dissolved in the broth. The above extraction with an organic solvent may be applied not only to the broth filtrate and supernatant but also to the culture broth as such. The precipitate or extract obtainable in the above manner hardly contains any amounts of unconsumed 11-hydroxylithocholic acid or/and a salt thereof or of byproducts, and may be recrystallized, if required, from aqueous methanol, for instance, to give a high-purity grade of 11-hydroxypregn-4-en-3-one-20-carbaldehyde.

11-Hydroxylithocholic acid which is employed as the substrate in the method of this invention can be derived from deoxycholic acid, for example by the process shown by the following reaction scheme:

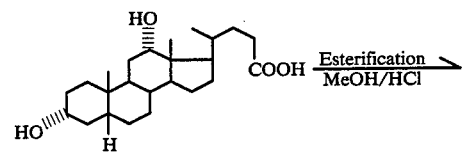

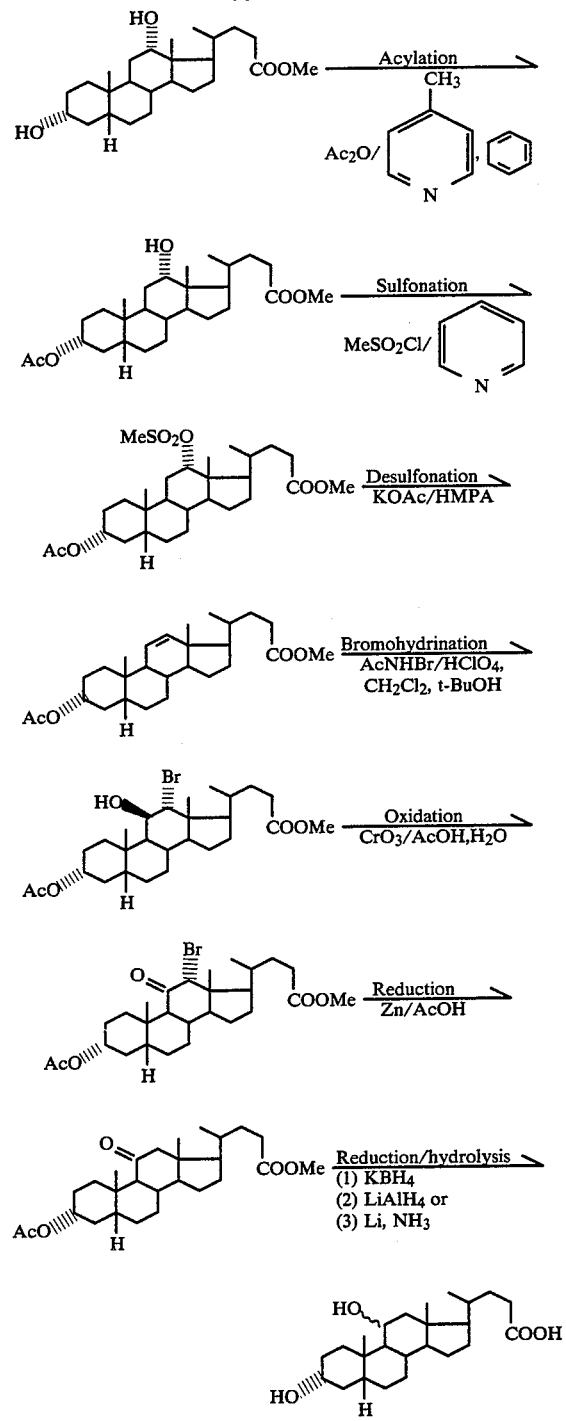

In the above formulas, Me means a methyl group, t-Bu means a tert-butyl group, Ac means an acetyl group, HMPA stands for hexamethylphosphorotriamide, and the wavy line ~ denotes that the indicated hydroxy group is either in the α- or in the β-configuration.

11β-Hydroxypregn-4-en-3-one-20-carbaldehyde and 11α-hydroxypregn-4-en-3-one-20-carbaldehyde, both of which are provided in accordance with this invention, can be converted, for example, to 11β-hydroxypregn-4-ene-3,20-dione or pregn-4-ene-3,11,20-trione via the routes illustrated and described below.

Reaction scheme (i):

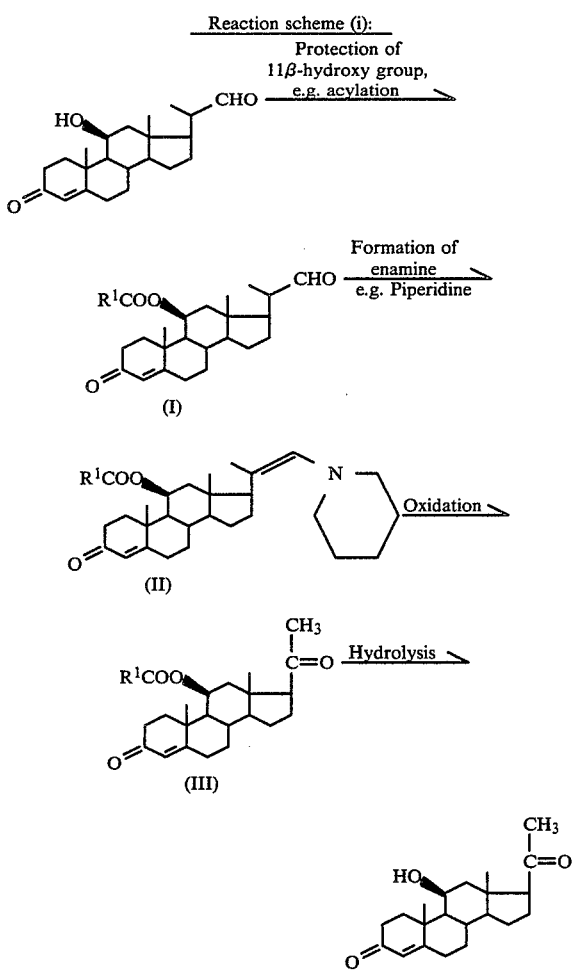

Protection of the hydroxy group in 11β-position of 11β-hydroxypregn-4-en-3-one-20-carbaldehyde is effected for example by acylation. Reaction of 11β-hydroxypregn-4-en-3-one-20-carbaldehyde with a carboxylic acid of general formula (IV)

$$R^1COOH \qquad (IV)$$

wherein $R^1$ is a methyl, trichloromethyl or trifluoromethyl group, or a reactive derivative thereof such as the acid halide or acid anhydride in the conventional manner yields an 11β-acyloxypregn-4-en-3-one-20-carbaldehyde of general formula (I). The reaction of 11β-hydroxypregn-4-en-3-one-20-carbaldehyde with chloride of a carboxylic acid (IV) which may be mentioned as a typical example is carried out in the presence of a tertiary amine such as triethylamine or pyridine. This reaction is preferably conducted in a solvent, which is exemplified by such preferred solvents as methylene chloride or chloroform, or mixtures thereof with benzene, toluene, ethyl acetate or the like. While this reaction is generally carried out at room temperature, it may be conducted at an elevated temperature up to about 60° C., if necessary. The reaction mixture is then washed with dilute hydrochloric acid, aqueous sodium hydrogen carbonate, and water, for instance, followed by drying. It is then distilled to remove low-boiling fractions, whereby the 11β-acyloxypregn-4-en-3-one-20-carbaldehyde of general formula (I) is obtained as a crude product. This crude product can be directly submitted to the next reaction. The formation of an enamine of an 11β-acyloxypregn-4-en-3-one-20-carbaldehyde is carried out by reacting the aldehyde with a secondary amine such as piperidine, pyrrolidine or morpholine. When piperidine is used as said secondary amine, the enamine of general formula (II) is produced. The secondary amine is used in a proportion of 1 to 2 molar equivalents relative to the 11β-acyloxypregn-4-en-3-one-20-carbaldehyde of general formula (I). The water byproduced in the course of this reaction is removed azeotropically from the reaction mixture using a solvent such as benzene or toluene. This reaction does not require a catalyst but it can be conducted in the presence of a catalyst such as p-toluenesulfonic acid. After the reaction, low-boiling fractions are distilled off under reduced pressure, whereby the enamine is obtained in crude form. This crude enamine can be used in the next reaction.

This enamine is oxidized with ozone or with chromic anhydride, pyridinium chlorochromate, sodium dichromate or the like to give an 11β-acyloxypregn-4-ene-3,20-dione of general formula (III). The oxidation reaction using chromic anhydride is generally carried out in the solvent pyridine. In this case, a mixture of chromic anhydride and pyridine is gradually added to a solution of the enamine in pyridine or, alternatively, a pyridine solution of the enamine is gradually added to a mixture of chromic anhydride and pyridine. This oxidation reaction is carried out at temperatures of about 0° C. to room temperature. Following the reaction, the reaction mixture is diluted with benzene, toluene or the like, the solid fraction is filtered off, and dilute hydrochloric acid is added to the filtrate. The mixture is extracted with benzene, toluene or the like, and the extract is distilled to remove low-boiling components. This procedure gives 11β-acyloxypregn-4-ene-3,20-dione in crude form. If necessary, this crude product is subjected to column chromatography on silica gel to give a high purity grade of 11β-acyloxypregn-4-ene-3,20-dione of general formula (III). This 11β-acyloxypregn-4-ene-3,20-dione is hydrolyzed in the conventional manner to 11β-hydroxypregn-4-ene-3,20-dione. By way of illustration, this hydrolysis reaction is conducted in a solvent such as methanol or ethanol and in the presence of potassium hydroxide, sodium hydroxide or the like at temperatures of from room temperature to the reflux temperature of the solvent used. After completion of this reaction, the reaction mixture is concentrated under reduced pressure and the concentrate is diluted with benzene, toluene or the like, washed with water, dilute hydrochloric acid or the like, dried and distilled to remove low-boiling components, whereby 11β-hydroxypregn-4-ene-3,20-dione is obtained in crude form. If necessary, this crude product can be purified by silica gel column chromatography.

In the process shown by the reaction scheme (i), 11α-hydroxypregn-4-ene-3,20-dione can be produced by using 11α-hydroxypregn-4-en-3-one-20-carbaldehyde in lieu of 11β-hydroxypregn-4-en-3-one-20-carbaldehyde.

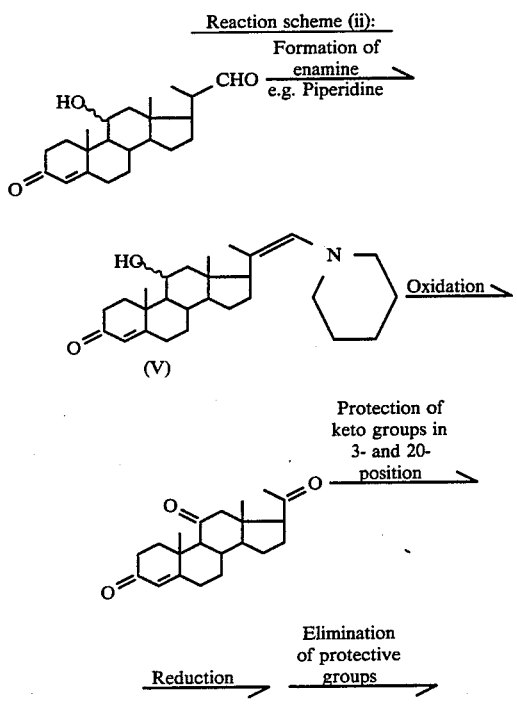

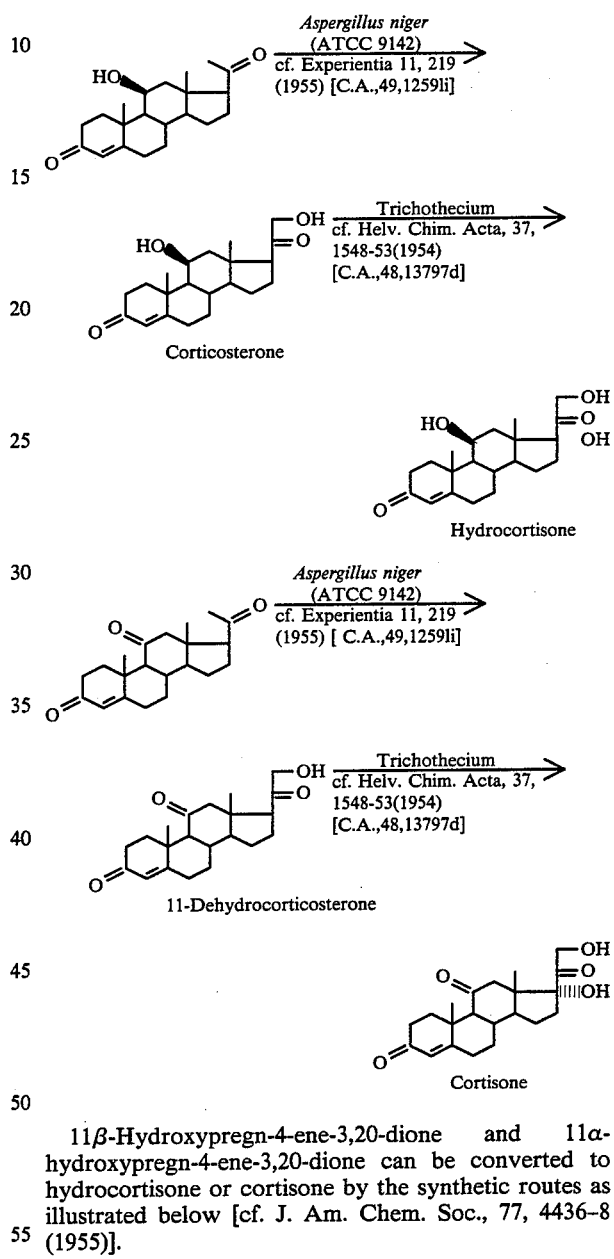

In the above formulas, the wavy line ~ has the same meaning as defined hereinbefore.

The formation of an enamine of 11-hydroxypregn-4-en-3-one-20-carbaldehyde is conducted in the same manner as the formation of the enamine according to reaction scheme (i) without prior protection of its 11-hydroxy group. When piperidine is used as said secondary amine, the enamine of general formula (V) is formed. This enamine is oxidized under the same conditions as those described for the oxidation according to reaction scheme (i) to give pregn-4-ene-3,11,20-trione.

Of this pregn-4-ene-3,11,20-trione, the 3- and 20-keto groups are protected in semicarbazone form with semicarbazide or in ketal form with diethylene glycol. The protected pregn-4-ene-3,11,20-trione is then reduced at its 11-keto group with potassium borohydride, followed by elimination of the protective groups in 3- and 20-positions in the presence of an acid, whereby 11β-hydroxypregn-4-ene-3,20-dione is obtained. The above elimination of protective groups is carried out in the presence of nitrous acid in the case of the semicarbazone form, or in the presence of p-toluenesulfonic acid, sulfuric acid or the like in the case of the ketal form.

11β-hydroxypregn-4-ene-3,20-dione and pregn-4-ene-3,11,20-trione as obtained by the processes according to the reaction schemes (i) and (ii) can be converted to hydrocortisone or cortisone by means of microorganisms.

11β-Hydroxypregn-4-ene-3,20-dione and 11α-hydroxypregn-4-ene-3,20-dione can be converted to hydrocortisone or cortisone by the synthetic routes as illustrated below [cf. J. Am. Chem. Soc., 77, 4436-8 (1955)].

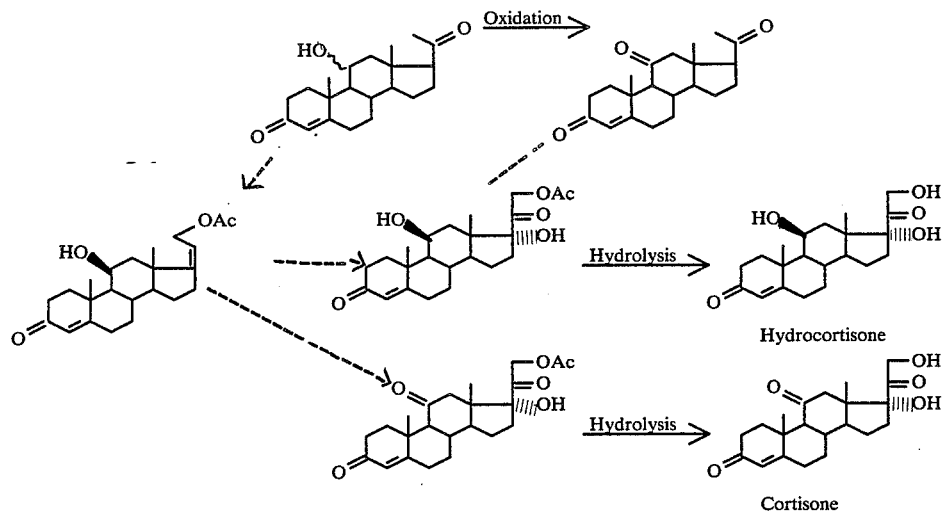

The following examples and reference examples illustrate the present invention in further detail but are not to be construed as limiting the scope thereof.

PREPARATION OF MUTANT

Preparation of the strain *Alcaligenes faecalis* D4020-K15

*Alcaligenes faecalis* D4020 was grown on a slant of medium 1 (composition: 0.5% deoxycholic acid, 0.05% sodium hydroxide, 0.5% peptone, 0.5% yeast extract, 0.5% sodium chloride and 1.5% agar). A loopful of the microorganism so grown was used to inoculate 10 ml of medium 2 (composition: 2% deoxycholic acid, 0.2% sodium hydroxide, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), and shake-cultured at 30° C. for 8–10 hours. A 0.3-ml-portion of the culture was added to 10 ml of medium 3 (composition: 0.5% deoxycholic acid, 0.05% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by incubation at 30° C. for 10–15 hours. The cells, which were in the logarithmic growth phase, were collected aseptically by filtration using a membrane filter (pore size: 0.45μ), washed with 20 ml of 0.1M phosphate buffer (pH 7.0) and suspended in 25 ml of the same buffer. To the suspension was added N-methyl-N'-nitro-N-nitrosoguanidine to a final concentration of 20 μg/ml. The mixture was shaken at 30° C. for 10–15 minutes. The cells so subjected to mutagenic treatment were collected by filtration using a membrane filter (pore size: 0.45μ), washed with 20 ml of 0.1M phosphate buffer (pH 7.0) and suspended in 20 ml of the same buffer. The resulting suspension was diluted with sterilized physiological saline solution and the dilution was applied to an agar plate made of medium 4 (composition: 0.5% deoxycholic acid, 0.05% sodium hydroxide, 0.2% ammonium nitrate, 0.1% potassium dihydrogen phosphate, 0.6% dipotassium hydrogen phosphate, 0.02% magnesium sulfate heptahydrate, 0.02% yeast extract and 1.5% agar) so that 500 to 1,000 colonies could appear on the plate. The incubation was then performed at 30° C. for 3–4 days. Among the colonies that had appeared, pin point colonies were transferred to a slant made of medium 1, and one loopful thereof was used to inoculate 10 ml of medium 5 (composition: 0.2% deoxycholic acid, 0.02% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by shake culture at 30° C. for 24 hours. The products in each culture obtained in this manner were examined by thin layer chromatography. A strain capable of selectively accumulating 12α-hydroxypregna-1,4-dien-3-one-20-carbaldehyde under the above cultural conditions was found and named *Alcaligenes faecalis* D4020-K15.

EXAMPLE

*Alcaligenes faecalis* D4020-K15 (FERM BP-204) was cultivated in the following manner. A medium (pH 8.0) was prepared by adding tap water to 0.5 g of 11β-hydroxylithocholic acid, 0.5 g of glycerol, 0.1 g of ammonium nitrate, 0.1 g of potassium dihydrogen phosphate, 0.6 g of dipotassium hydrogen, 0.02 g of magnesium citrate, 0.02 g of yeast extract, 0.1 g of sodium hydroxide, to a volume of 100 ml. This medium was filled into a 500 ml Sakaguchi flask and steam-sterilized at 120° C. for 15 minutes. The flask was inoculated with 10 ml of a 1-day seed culture of the above-mentioned strain grown in the same medium as above in a test tube under shaking, and the inoculated flask was incubated at 30° C. under shaking for 2 days. The culture broth was centrifuged at 2000 rpm for 1 minute, followed by decantation to separate the supernatant containing the cells from the precipitate formed during cultivation. The precipitate was rinsed with water and dried to give 0.29 g of 11β-hydroxypregn-4-en-3-one-20-carbaldehyde.

A portion of this 11β-hydroxypregn-4-en-3-one-20-carbaldehyde was taken and dissolved in methanol to prepare a 2% solution and 20 μl of this solution was injected into a high performance liquid chromatograph equipped with a μBondapak C-18 column (Model HLC-GPC-244 manufactured by Waters Associates in U.S.A.). A 25:75 (by volume) mixture of water and methanol (pH 4.0) was used as the mobile phase at a flow rate of 1 ml/minute. The detection was made by the refractive index method and the chromatographic peak areas were measured with an integrator (Shimadzu Chromato-Pack C-RIA manufactured by Shimadzu Corporation in Japan). The purity of 11β-hydroxypregn-4-en-3-one-20-carbaldehyde as found from the peak area ratio was 90%.

A portion of the above 11β-hydroxypregn-4-en-3-one-20-carbaldehyde was dissolved in 10% water-methanol and after removal of insolubles by filtration, was recrystallized from water-methanol, whereby a pure product with an HPLC purity of 95% was obtained.

The identification of 11β-hydroxypregn-4-en-3-one-20-carbaldehyde was made on the basis of the following physicochemical constants.

Melting point: 147°–149° C.

FD-mass spectrum (m/z): [M]+344

NMR spectrum (90 MHz) $\delta_{HMS}^{CDCl_3}$: 0.97 (3H, s); 1.08 (3H, d); 1.42 (3H, s); 4.38–4.23 (1H, m); 5.63 (1H, s); 9.55 (1H, d)

IR spectrum (KBr, cm$^{-1}$): 1610, 1650, 1720, 3400

What is claimed is:

1. A compound of the formula

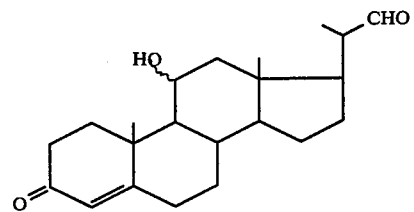

wherein the wavy line ~ denotes that the indicated hydroxy group is either in the α- or in the β-configuration.

2. A compound of claim 1, which is 11β-hydroxypregn-4-en-3-one-20-carbaldehyde of the formula

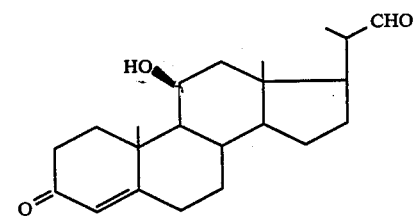

* * * * *